United States Patent
Glasky

(10) Patent No.: US 6,303,617 B1
(45) Date of Patent: Oct. 16, 2001

(54) SEROTONIN-LIKE 9-SUBSTITUTED HYPOXANTHINE AND METHODS OF USE

(75) Inventor: Alvin J. Glasky, Tustin, CA (US)

(73) Assignee: Neotherapeutics, Inc., Irvine, CA (US)

( * ) Notice: Subject to any disclaimer, the term of this patent is extended or adjusted under 35 U.S.C. 154(b) by 0 days.

(21) Appl. No.: 09/304,728

(22) Filed: May 4, 1999

Related U.S. Application Data

(60) Provisional application No. 60/084,023, filed on May 4, 1998.

(51) Int. Cl.[7] .................. C07D 473/30; A61K 31/522; A61P 3/04; A61P 3/06; A61P 25/24
(52) U.S. Cl. .................................. 514/262; 544/276
(58) Field of Search .................. 514/262; 544/276

(56) References Cited

U.S. PATENT DOCUMENTS

| | | | |
|---|---|---|---|
| 3,300,380 | 1/1967 | Gray et al. | 167/65 |
| 3,666,856 | 5/1972 | Elion et al. | 424/120 |
| 4,035,486 | 7/1977 | Laborit | 524/178 |
| 4,138,562 | 2/1979 | Vince | 544/326 |
| 4,221,794 | 9/1980 | Simon et al. | 424/253 |
| 4,221,909 | 9/1980 | Simon et al. | 544/265 |
| 4,221,910 | 9/1980 | Giner-Sorolla | 544/265 |
| 4,315,920 | 2/1982 | Schaeffer et al. | 424/180 |
| 4,340,726 | 7/1982 | Simon et al. | 536/17.4 |
| 4,347,360 | 8/1982 | Ogilvie | 544/276 |
| 4,451,478 | 5/1984 | Simon et al. | 424/273 |
| 4,643,992 | 2/1987 | Goodman et al. | 514/45 |
| 4,952,693 | 8/1990 | Sircar et al. | 544/255 |
| 5,023,294 | 6/1991 | Goto et al. | 514/46 |
| 5,091,432 | * 2/1992 | Glasky | 514/262 |
| 5,093,318 | 3/1992 | Goodman et al. | 514/45 |
| 5,187,162 | 2/1993 | Marangos et al. | 514/46 |
| 5,237,051 | 8/1993 | Garbers et al. | 530/350 |
| 5,256,677 | 10/1993 | Sham et al. | 514/351 |
| 5,376,642 | 12/1994 | Yarchoan et al. | 514/45 |
| 5,447,939 | 9/1995 | Glasky et al. | 514/310 |
| 5,565,437 | 10/1996 | Marquez et al. | 514/45 |
| 5,595,901 | 1/1997 | Rocancourt et al. | 435/183 |
| 5,801,159 | 9/1998 | Miller et al. | 514/45 |
| 5,801,184 | 9/1998 | Glasky et al. | 514/310 |
| 5,948,771 | 9/1999 | Danziger | 514/185 |
| 6,027,936 | 2/2000 | Glasky | 435/310 |

OTHER PUBLICATIONS

N.W. Tietz, ed., "Clinical Chemistry" (W.B. Saunders Co., Philadelphia, 1986), pp. 882–886 (Exhibit 11).

G.A. Lyles & B.A. Callingham, "The Effects of Thyroid Hormones on Monoamine Oxidase in the Rat Heart," *J. Pharm. Pharmacol.* 26:921–930 (1974) (Exhibit 12).

(List continued on next page.)

Primary Examiner—Mukund J. Shah
Assistant Examiner—Thomas C McKenzie
(74) Attorney, Agent, or Firm—Oppenheimer Wolff & Donnelly LLP

(57) ABSTRACT

Novel 9-substituted hypoxanthine derivatives with unexpected physiological effects are disclosed. These compounds are of formula (I) where n is an integer from 1 to 6, $R_1$ is selected from the group consisting of H, COOH, and $COOW_1$, where $W_1$ is selected from the group consisting of lower alkyl, amino, and lower alkylamino, and $R_2$ is selected from the group consisting of H and OH. Among these compounds are N-(2-(5-hydroxyindol-3-yl)ethyl-3-6-oxyhydropurin-9-yl)propanamide, N-2-(indol-3-yl)ethyl)-3-(6-oxyhydropurin-9-yl)propanamide and N-(1-carboxyl)-(2-(5-hydroxyindol-3-yl)ethyl-3-(6-oxyhydropurin-9-yl) propanamide. These compounds have a number of utilities, including inhibition of the activity of monoamine oxidases, treating obesity, lowering serum cholesterol, and increasing the level of HDL cholesterol. Also disclosed are pharmaceutical compositions and methods of use of the derivatives to treat a number of disorders or conditions.

26 Claims, 4 Drawing Sheets

OTHER PUBLICATIONS

P.J. Middlemiss et al., "AIT–082, a Unique Purine Derivative, Enhances Nerve Growth Factor Mediated Neurite Outgrowth from PC12 Cells," *Neurosci. Lett.* 199: 131–134 (1995).

K.L. Audus et al., "Brain Uptake of Drugs: the Influence of Chemical and Biological Factors," *Adv. Drug Res.* 23: 1–64 (1992).

W.A. Banks & A.J. Kastin, "Measurement of Transport of Cytokines Across the Blood–Brain Barrier," *Meth. Neurosci.* 16: 67–77 (1993).

A.L. Betz, "Identification of Hypoxanthine Transport and Xanthine Oxidase Activity in Brain Capillaries," *J. Neurochem.* 44: 574–579 (1985).

F.G. Blasberg et al., "Transport of α–Aminoisobutyric Acid Across Brain Capillary and Cellular Membranes," *J. Cereb. Blood Flow Metab.* 3: 8–32 (1983).

E.M. Cornford & W.H. Olendorf, "Independent BloodBrain Barrier Transport Systems for Nucleic Acid Precursors," *Biochim. Biophys. Acta* 394: 211–219 (1975).

A.J. Glasky et al., "Effect of AIT–082, a Purine Analog, on Working Memory in Normal and Aged Mice," *Pharmacol. Biochem. Behav.* 47: 325–329 (1994).

A.J. Glasky et al., "Neurotrophins, Growth Factors and Mimetic Agents as Neuroprotectors in the Treatment of Alzheimer's Disease" in *Alzheimer Disease: From Molecular Biology to Therapy* (R. Becker & E. Giacobini, eds., Birkhäuser, Boston, 1996), pp. 119–124.

E.G. Gutierrez et al., "Murine Tumor Necrosis Factor Alpha Is Transported from Blood to Brain in the Mouse," *J. Neuroimmunol.* 47: 169–176 (1993).

M. Hosokawa & M. Ueno, "Aging of Blood–Brain Barrier and Neuronal Cells of Eye and Ear in SAM Mice," *Neurobiol. Aging* 20: 117–123 (1999).

M.D. Johnson & B.D. Anderson, "Localization of Purine Metabolizing Enzymes in Bovine Brain Microvessel Endothelial Cells: An Enzymatic Blood–Brain Barrier for Dideoxynucleosides?," *Pharm. Res.* 13: 1881–1886 (1996).

A.D. Mooradian, "Effect of Aging on the Blood–Brain Barrier," *Neurobiol. Aging* 9: 31–39 (1988).

W. Pan et al., "Permeability of the Blood–Brain Barrier to Neurotrophins," *Brain Res.* 788: 87–94 (1998).

W.M. Pardridge, "CNS Drug Design Based on Principles of Blood–Brain Barrier Transport," *J. Neurochem.* 70: 1781–1792 (1998).

J.F. Poduslo et al., "Macromolecular Permeability Across the Blood–Nerve and Blood–Brain Barriers," *Proc. Natl. Acad. Sci. USA* 91: 5705–5709 (1994).

J.F. Poduslo & G.L. Curran, "Permeability at the BloodBrain Barrier and Blood–Nerve Barriers of the Neurotrophic Factors: NGF, CNTF, NT–3, BDNF," *Mol. Brain Res.* 36: 280–286 (1996).

J.J. Ramirez et al., "AIT–082 Accelerates Septodentate Sprouting After Unilateral Entorhinal Cortex Lesion in Rats," *Soc. Neurosci. Abstr.* 24: 1942 (1998).

G.N. Shah & A.D. Mooradian, "Age–Related Changes in the Blood–Brain Barrier," *Exp. Gerontol.* 32: 501–519 (1997).

I. Skoog et al., "A Population Study on Blood–Brain Barrier Function in 85–Year–Olds: Relation to Alzheimer's Disease and Vascular Dementia," *Neurology* 50: 966–971 (1998).

R. Spector, "Hypoxanthine Transport Through the Blood-Brain Barrier," *Neurochem. Res.* 12: 791–796 (1987).

R. Spector, "Hypoxanthine Transport and Metabolism in the Central Nervous System," *J. Neurochem.* 50: 969–978 (1988).

D. Triguero et al., "Capillary Depletion Method for Quantitation of Blood–Brain Barrier Transport of Circulating Peptides and Plasma Proteins," *J. Neurochem.* 54: 1882–1888 (1990).

W.A. Banks et al., "Measurement of Efflux Rates from Brain to Blood" in *Methods in Molecular Biology, Neuropeptide Protocols* (G.B. Irvine & C.H. Williams, eds., Humana Press, Totowa, NJ, 1997), pp. 353–360.

M.P. Rathbone et al., "Physiology and Pharmacology of Natural and Synthetic Nonadenine–Based Purines in the Nervous System," *Drug Develop. Res.* 45: 356–372 (1998).

M.P. Rathbone et al., AIT–082 as a Potential Neuroprotective and Regenerative Agent in Stroke and Central Nervous System Injury, *Exp. Opin. Invest. Drugs* 8: 1255–1262 (1999).

W.A. Banks et al., "Effects of Wheatgerm Agglutinin and Aging on the Regional Brain Uptake of HIV–1 gp120," *Life Sci.* 65: 81–89 (1999).

J.S. Bintner et al., "AIT–082, a Hypoxanthine Derivative, Prevents Much of the Decrease in Cerebellar Neuron ATP Following Glutamate Exposure," *Soc. Neurosci.* 25: 2131 (1999) (abstract).

R. Huang et al., "Enhancement of Neuronal Cell Excitability by AIT–082 in Rat Hippocampal Neurons and Its Effects on Second Messenger Systems," *Soc. Neurosci.* 24: 1941 (1998) (abstract).

O.Chu–LaGraff et al., "Effect of AIT–082 on Brain NGF mRNA Levels and Transport of AIT–082 Across the Blood-Brain Barrier," *Soc. Neurosci.* 24: 1941 (1998) (abstract).

F. Caciagli et al., "The Hypoxanthine Derivative AIT–082 Protects Against Neurotoxicity in Vitro and in Vivo," *Soc. Neurosci.* 24: 1941 (1998) (abstract).

B.H.J. Juurlink et al., "The Hypoxanthine Analogue AIT–082 Promotes Neurite Formation and Regeneration in Cultured Hippocampal Neurons," *Soc. Neurosci.* 24: 1941 (1998) (abstract).

E.M. Taylor et al., "$^{14}$C–AIT082 Crosses the Blood–Brain Barrier and Is Pumped Out of Brain by a Probenecid– and Verapamil–Sensitive Mechanism," *Soc. Neurosci.* 25: 1758 (1999) (abstract).

F. Caciagli et al., "The Hypoxanthine Analogue AIT–082 Mimics the Activity of Guanosine in Affecting Extracellular Adenosine Breakdown and Glutamate Reuptake in Rat Cultured Astrocytes," *Soc. Neurosci.* 25: 1195 (1999) (abstract).

R. Ciccarelli et al., "Guanosine and Related Drugs Stimulate the Production of Neurotrophic Factors from Rat Cultured Astrocytes by Involving Mitogen–Activated Protein Kinase Pathway," *Soc. Neurosci.* 25: 1013 (1999) (abstract).

P.J. Middlemiss et al., "The Synthetic Purine AIT–082 Enhances Recovery After Acute Spinal Cord Crush Injury in Rats," *Soc. Neurosci.* 25: 1002 (1999) (abstract).

P. Di Iorio et al., "The Hypoxanthine Derivative AIT–082 Is Protective Agianst NMDA– or Kainic Acid–Induced Rat Hippocampal Neurotoxicity in Vivo," *Soc. Neurosci.* 25: 756 (1999) (abstract).

A.G. Gittis & J.R. Puzuasky, "AIT–082 Improves Memory Performance in a Non–Match–to–Sample Task in Rats," *Soc. Neurosci.* 25: 62 (1999) (abstract).

* cited by examiner

SEROTONIN-LIKE 9-SUBSTITUTED HYPOXANTHINE AND METHODS OF USE

CROSS-REFERENCES

This application claims priority from Provisional Application Serial No. 60/084,023, entitled "Novel Serotonin-Like 9-Substituted Hypoxanthine and Method of Use," by Alvin J. Glasky, filed May 4, 1998, incorporated herein in its entirety by this reference.

FIELD OF THE INVENTION

The present invention is broadly directed to purine based compounds. More particularly, the present invention is directed to a novel purine analog having activity involving the serotonin neurotransmitter system in addition to other physiological activities and to associated methods of use.

BACKGROUND OF THE INVENTION

The efficacy of many contemporary pharmaceutical compounds intended to treat neurological and physiological conditions is limited by their inability to cross the blood-brain barrier. As a result, large molecules that may have neurological activity cannot be administered orally or through injection into the bloodstream because the blood-brain barrier serves as a filter to keep these molecules from leaving the bloodstream and entering the brain and spinal cord. Currently there are three alternative approaches to achieving blood-brain barrier access. The first is to introduce pharmaceutical compounds by direct injection into the brain through the skull. While such treatments have demonstrated some success the possibility of infection coupled with the complexity and expense of such procedures have limited their practical usefulness. Additionally, there is resistance among many patients to the administration of such injections directly into the skull. The second approach involves the utilization of chemical agents which temporarily break down the blood-brain barrier in order to allow molecules to enter the central nervous system. At present, this approach is in the very early stages of development and carries with it the potential for allowing molecules of all sizes (including undesirable compounds) to cross the blood-brain barrier. This approach, unless and until it can be refined to allow for greater selectivity in crossing the blood-brain barrier, carries with it serious risks. The third approach, pioneered by the present inventor, involves developing small molecules which can mimic the activities of bioactive molecules yet can pass through the blood-brain barrier following oral administration or administration through injection into the bloodstream.

Therefore, there is a need for the development of small molecules that can mimic physiological activities of bioactive molecules and can cross the blood-brain barrier efficiently without requiring complete degradation of the blood-brain barrier.

It is accordingly an object of the present invention to provide such compounds which can either mimic the actions of molecules normally unable to cross the blood-brain barrier or which can stimulate other, unexpected physiological activities.

It is an additional object of the present invention to produce pharmaceutical medicaments configured from such compounds and to provide methods for using these pharmaceutical compositions to treat a variety of physiological, neurological, and psychological disorders and disease conditions.

SUMMARY

I have found that novel 9-substituted hypoxanthine derivatives have unexpected properties and have monoamine oxidase inhibitor activity.

One embodiment of the present invention is a 9-substituted hypoxanthine derivative of formula (I)

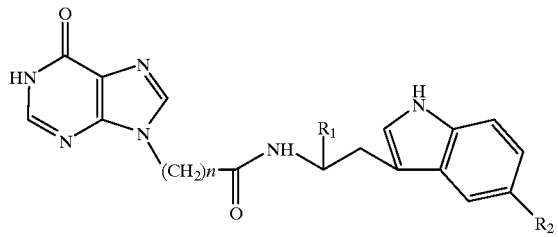

(I)

where n is an integer from 1 to 6, $R_1$ is selected from the group consisting of H, COOH, and $COOW_1$, where $W_1$ selected from the group consisting of lower alkyl, amino, and lower alkylamino, and $R_2$ is selected from the group consisting of H and OH.

Preferably, n is 2. When n is 2, one particularly preferred 9-substituted hypoxanthine derivative is N-(2-(5-hydroxyindol-3-yl)ethyl)-3-(6-oxohydropurin-9-yl) propanamide, where n is 2, $R_1$ is H, and $R_2$ is OH; this compound is designated AIT-202. Another particularly preferred 9-substituted hypoxanthine derivative is N-(2-(indol-3-yl)ethyl)-3-(6-oxohydropurin-9-yl)propanamide, where n is 2, $R_1$ is H, and $R_2$ is H; this compound is designated AIT-072. Still another particularly preferred 9-substituted hypoxanthine derivative is N-(1-carboxyl)-(2-(5-hydroxyindol-3-yl)ethyl-3-(6-oxohydropurin-9-yl) propanamide, where n is 2, $R_1$ is COOH, and $R_2$ is OH; this compound is designated AIT-111.

Another aspect of the present invention is a pharmaceutical composition comprising:

(1) an effective amount of a 9-substituted hypoxanthine derivative according to the present invention as described above; and (2) a pharmaceutically acceptable carrier.

Yet another aspect of the present invention is a method of treating a disease or condition in a mammal treatable by inhibiting the activity of a monoamine oxidase comprising the step of administering an effective amount of a 9-substituted hypoxanthine derivative according to the present invention to the mammal.

Still another aspect of the present invention is a method of treating obesity in a mammal comprising the step of administering an effective amount of a 9-substituted hypoxanthine derivative according to the present invention to the mammal.

An additional aspect of the present invention is a method of lowering the level of serum cholesterol in a mammal comprising the step of administering an effective amount of a 9-substituted hypoxanthine derivative according to the present invention to the mammal.

Yet another aspect of the present invention is a method for increasing the level of HDL cholesterol in the blood serum of a mammal comprising the step of administering an effective amount of a 9-substituted hypoxanthine according to the present invention to the mammal.

BRIEF DESCRIPTION OF THE DRAWINGS

The following invention will become better understood with reference to the specification, appended claims, and accompanying drawings, where:

DETAILED DESCRIPTION

Figure 1:
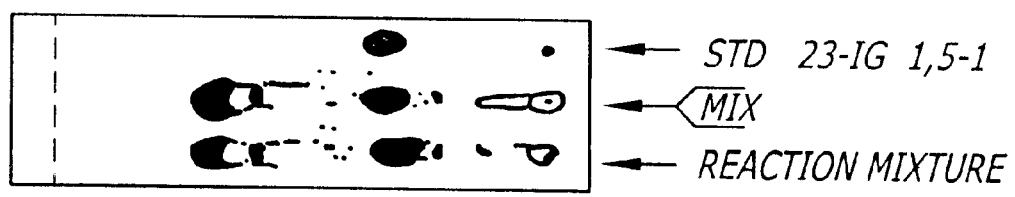
FIG. 1 is a diagram of a thin-layer chromatogram of the crude product from the synthesis of N-(2-(5-hydroxyindol-3-yl)ethyl)-3-(6-oxohydropurin-9-yl)propanamide of Example 2; chromatography was performed in 20% methanol in ethyl acetate, with visualization by ultraviolet light.

These and other objects are achieved by the novel pharmaceutical composition and associated methods of the present invention which provide a novel 9-substituted hypoxanthine based composition which is able to cross the blood-brain barrier and which can impact a variety of physiological and psychological systems.

In general, 9-substituted hypoxanthine-based compounds according to the present invention have the structure shown in Formula (I), where n is an integer from 1 to 6, $R_1$ is selected from the group consisting of H, COOH, and $COOW_1$, where $W_1$ selected from the group consisting of lower alkyl, amino, and lower alkylamino, and $R_2$ is selected from the group consisting of H and OH. "Lower alkyl," in the context of this disclosure, means a saturated alkyl group of from 1 to 6 carbon atoms. It is generally preferred that n is 2.

Three particularly preferred compounds according to the present invention are: (1) N-(2-(5-hydroxyindol-3-yl)ethyl)-3-(6-oxohydropurin-9-yl)propanamide, where n=2, $R_1$ is H, and $R_2$ is OH, designated AIT-202; (2) N-(2-(indol-3-yl) ethyl)-3-(6-oxohydropurin-9-yl)propanamide, where n=2, $R_1$ is H, and $R_2$ is H, designated AIT-072; and (3) N-(1-carboxyl)-(2-(5-hydroxyindol-3-yl)ethyl-3-(6-oxohydropurin-9-yl)propanarnide, where n=2, $R_1$ is COOH, and $R_2$ is OH, designated AIT-111.

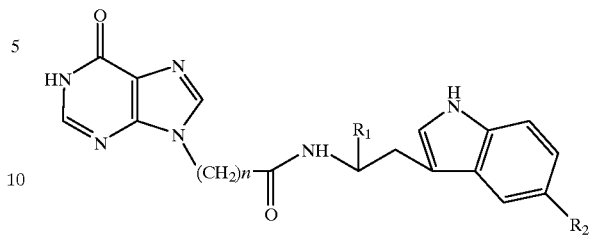

(I)

More specifically, the present invention provides a novel purine analog, N-(2-(5-hydroxyindol-3-yl)ethyl)-3-(6-oxohydropurin-9-yl)propanamide, which, in a broad aspect, can be viewed as analogous to hypoxanthine chemically linked to a serotonin analog. Surprisingly, this compound exhibits functional features of both hypoxanthine and serotonin. As a result, it is able to pass through the blood-brain barrier following oral administration or administration through injection into the bloodstream and, because of the structural similarity of a portion of this compound to serotonin, it exhibits physiological activity involving the serotonin neurotransmitter system. Thus, it can function as an anti-depressant compound and in the treatment of obesity. Additionally, and quite unexpectedly, it also exhibits the ability to lower cholesterol levels and to increase HDL levels in animals. Exemplary dosages in accordance with the teachings of the present invention range from 0.01 mg/kg to 60 mg/kg, though alternative dosages are contemplated as being within the scope of the present invention.

Compounds according to the present invention, including N-(2-(5-hydroxyindol-3-yl)ethyl)-3-(6-oxohydropurin-9-yl) propanamide, can be synthesized by a number of procedures. In general, these procedures involve coupling a purine moiety and a serotonin moiety. One of these moieties bears the linker that couples the purine moiety and the serotonin moiety.

One particularly suitable procedure involves: (1) formation of a N-hydroxysuccinimide (NHS) ester of a derivative of hypoxanthine that has a carboxyl moiety substituted at the 9-position of hypoxanthine using a coupling agent such as a carbodiimide; and (2) reacting the NHS ester directly with the serotonin to link the hypoxanthine moiety with the serotonin moiety through the appropriate linker. This method is further described in Examples 1 and 2 for the synthesis of N-(2-(5-hydroxyindol-3-yl)ethyl)-3-(6-oxohydropurin-9-yl)propanamide. The method can be used for synthesis of other compounds according to the present invention by varying the starting materials used.

The use of carbodiimides as coupling agents to form such NHS esters is well known in the art. A preferred carbodiimide is dicyclohexyl carbodiimide (DCC), but other carbodiimides are well known in the art and can be used. DCC is particularly suitable if the coupling reactions is to be performed in an organic medium. If the coupling reaction is to be performed in an aqueous medium, other, water-soluble carbodiimides such as 1-ethyl-3-(3-dimethylaminopropyl) carbodiimide (EDC) and 1-cyclohexyl-3-(2-morpholinyl-4-ethyl)carbodiimide (CMC) can alternatively be used.

Suitable dosages can be chosen by the treating physician by taking into account such factors as the size, weight, age, and sex of the patient, the physiological state of the patient, the severity of the condition for which the compound is being administered, the response to treatment, the type and quantity of other medications being given to the patient that might interact with the compound, either potentiating it or inhibiting it, and other pharmacokinetic considerations such as liver and kidney function.

Another aspect of the present invention is pharmaceutical compositions. A pharmaceutical composition according to the present invention comprises:

(1) a 9-substituted hypoxanthine-based compounds according to the present invention, as described above; and (2) a pharmaceutically acceptable carrier.

Preferably, the 9-substituted hypoxanthine-based compound is N-(2-(5-hydroxyindol-3-yl)ethyl)-3-(6-oxohydropurin-9-yl)propanamide.

The pharmaceutically acceptable carrier can be chosen from those generally known in the art, including, but not limited to, human serum albumin, ion exchangers, alumina, lecithin, buffer substances such as phosphates, glycine, sorbic acid, potassium sorbate, and salts or electrolytes such as potassium sulfate. Other carriers can be used.

Yet another aspect of the present invention is a method of treating a disease or condition in a mammal treatable by inhibiting the activity of a monoamine oxidase. The method comprises the step of administering an effective amount of the 9-substituted hypoxanthine derivative of the present invention to the mammal. The amount that is an effective amount can be determined from enzyme assays as an amount that produces a detectable inhibition of either monoamine oxidase A or monoamine oxidase B or both enzymes in the enzyme assay used in Example 3.

The most effective mode of administration and dosage regimen for the 9-substituted hypoxanthine derivatives as used in the methods in the present invention depend on the severity and course of the disease, the patient's health, the response to treatment, other drugs being administered and the response to them, pharmacokinetic considerations such as the condition of the patient's liver and/or kidneys that can affect the metabolism and/or excretion of the administered 9-substituted hypoxanthine derivatives, and the judgment of the treating physician. According, the dosages should be titrated to the individual patient.

Among the diseases and conditions for which monoamine oxidase inhibitors are clinically indicated are psychological and psychiatric conditions such as depression, panic disorders, and obsessive-compulsive disorder; chronic pain disorders such as diabetic and other peripheral neuropathic syndromes and fibromyalgia; peptic ulcer and irritable bowel syndrome; chronic fatigue; cataplexy; sleep apnea; migraine, and Parkinson's Disease. Such monoamine oxidase inhibitors may also be useful for other conditions.

The mammal can be a human or another socially or economically important mammal such as a dog, a cat, a horse, a cow, a pig, or a sheep. The method of the present invention is not limited to treatment of humans.

Additionally, as detailed in Example 4, compounds according to the present invention can also be used for control of obesity. The method comprises the step of administering an effective amount of the 9-substituted hypoxanthine derivative of the present invention to the mammal. The amount that is an effective amount can be determined from monitoring the weight of the mammal; guidance as to the effective amount is also provided by Example 4.

The most effective mode of administration and dosage regimen for the 9-substituted hypoxanthine derivatives as used in the methods in the present invention depend on the severity and course of the obesity to be treated, the patient's health, the response to treatment, the patient's diet, the patient's level of exercise, other drugs being administered and the response to them, pharmacokinetic considerations such as the condition of the patient's liver and/or kidneys that can affect the metabolism and/or excretion of the administered 9-substituted hypoxanthine derivatives, and the judgment of the treating physician. According, the dosages should be titrated to the individual patient.

The mammal can be a human or another socially or economically important mammal such as a dog, a cat, a horse, a cow, a pig, or a sheep. The method of the present invention is not limited to treatment of humans.

Yet another aspect of the present invention is a method for use of the compounds of the present invention in reducing serum cholesterol. The method comprises the step of administering an effective amount of the 9-substituted hypoxanthine derivative of the present invention to the mammal. The amount that is an effective amount can be determined from assay of cholesterol levels in serum. Methods for the determination of serum cholesterol are well known in the art, and typically involve enzymatic reactions, beginning with the hydrolysis of cholesteryl esters to produce free cholesterol and then the oxidation of cholesterol with cholesterol oxidase to yield cholest-4-ene-3-one and hydrogen peroxide. Various methods can then be used to detect either the molecular oxygen consumed or the hydrogen peroxide produced. Such methods are described, for example, in N. W. Tietz, ed., "Clinical Chemistry" (W.B. Saunders Co., Philadelphia, 1986), pp. 882–886, incorporated herein by this reference.

The most effective mode of administration and dosage regimen for the 9-substituted hypoxanthine derivatives as used in the methods in the present invention depend on the cholesterol level of the patient, the patient's health, the response to treatment, the patient's diet, the patient's level of exercise, other drugs being administered and the response to them, pharmacokinetic considerations such as the condition of the patient's liver and/or kidneys that can affect the metabolism and/or excretion of the administered 9-substituted hypoxanthine derivatives, and the judgment of the treating physician. Additional guidance is also given in Example 5. Accordingly, the dosages should be titrated to the individual patient.

The mammal can be a human or another socially or economically important mammal such as a dog, a cat, a horse, a cow, a pig, or a sheep. The method of the present invention is not limited to treatment of humans.

Yet another aspect of the present invention is a method for increasing the level of HDL cholesterol in the blood serum of a mammal comprising the step of administering an effective amount of a 9-substituted hypoxanthine derivative according to the present invention to the mammal. The amount that is an effective amount can be determined from assay of HDL cholesterol levels in serum. HDL cholesterol can be determined by selective precipitation of VLDL and LDL with various polyanions, e.g., heparin and manganese chloride, followed by measurement of the cholesterol concentration in the supernatant containing the HDL. Other methods are also known in the art.

The most effective mode of administration and dosage regimen for the 9-substituted hypoxanthine derivatives as used in the methods in the present invention depend on the HDL cholesterol level of the patient, the patient's health, the response to treatment, the patient's diet, the patient's level of exercise, other drugs being administered and the response to them, pharmacokinetic considerations such as the condition of the patient's liver and/or kidneys that can affect the metabolism and/or excretion of the administered 9-substituted hypoxanthine derivatives, and the judgment of the treating physician. According, the dosages should be titrated to the individual patient.

The mammal can be a human or another socially or economically important mammal such as a dog, a cat, a horse, a cow, a pig, or a sheep. The method of the present invention is not limited to treatment of humans.

The invention is illustrated by the following Examples. These examples are provided for exemplification only and are not intended to limit the invention.

EXAMPLE 1

Condensation of 3-(6-Oxohydropurin-9-yl) Propanoic Acid with N-Hydroxysuccinimide As a first step in the synthesis of N-(2-(5-hydroxyindol-3-yl)ethyl)-3-(6-oxohydropurin-9-yl)propanamide, a derivative of hypoxanthine, 3-(6-oxohydropurin-9-yl)propanoic acid, was activated by condensation with N-hydroxysuccinimide (NHS). The hypoxanthine derivative, 3-(6-oxohydropurin-9-yl) propanoic acid (30 g) was reacted with 23.24 g of NHS and 35.7 g of the coupling agent dicyclohexylcarbodiimide (DCC) in 550 ml of dry dimethylformamide (DMF). The resulting mixture was heated with magnetic stirring in an atmosphere of argon in an oil bath (bath temperature 85–90° C.) for 4 hours. The reaction mixture was used as such for the reaction of Example 2.

EXAMPLE 2

Synthesis of N-(2-(5-Hydroxyindol-3-yl)ethyl)-3-(6-oxohydropurin-9-yl)propanamide The serotonin analogue N-(2-(5-hydroxyindol-3-yl) ethyl)-3-(6-oxohydropurin-9-yl)propanamide was synthesized by reacting the reaction mixture resulting from Example 1 directly with serotonin to form the amide link. Serotonin hydrochloride (36.8 g) was magnetically stirred in a 500 ml flask with 100 ml dry DMF. To the suspension, 36 ml dry triethylamine was added. After a few minutes, the mixture was added to the reaction mixture obtained from Example 1. The serotonin flask was rinsed with 50 ml additional dry DMF and added to the reaction mixture. Heating at an oil bath temperature of 85–90° C. with stirring was continued for 2 hours. Within 15–20 minutes, the white slurry became almost homogeneous with a brown color with some turbidity. After 2 hours, thin-layer chromatography was performed in a solvent of 30% methanol in ethyl acetate with visualization by ultraviolet light. The results are shown in FIG. 1.

The reaction mixture was cooled to room temperature and then further cooled in an ice/water bath for 30 minutes. The precipitated dicyclohexylurea was filtered off and saved. The filtrate was evaporated to dryness (~120 g).

The evaporated filtrate was disolved in ~1000 ml methyl alcohol and to it 200 g $SiO_2$ was added. The mixture was evaporated to a dry powder and this was added on the top of a column made from 1.5 kg $SiO_2$ gel in ethanol. The column was eluted with the following sequence of solvents: (1) 4 liters of 5% methanol in ethyl acetate in 1-liter fractions; (2) 14 liters of 10% methanol in ethyl acetate in 1-liter fractions; (3) 10 liters of 25% methanol in ethyl acetate in 1-liter fractions; (4) 24 liters of a 2:1 mixture of ethyl acetate and methanol in 2-liter fractions; and (5) 18 liters of a 1:1 mixture of ethyl acetate and methanol in 1-liter fractions. Solvent flow and elution was quite slow as the product, deposited as a solid on the top of the column, was sparingly soluble in the eluting solvent system. The desired product started to elute at solvent (4) (ethyl acetate:methanol, 2:1). Each fraction was checked by thin-layer chromatography in 30% methanol in ethyl acetate. The fractions containing the desired material were pooled together and evaporated under rotary evaporation in a large evaporator. When the volume was reduced to about 1.5 liters, solid crystals that appeared were separated. The crystals were filtered and dried at 50° C. overnight under service line vacuum. The yield was 24 g. The melting point as 240–242° C. (sharp). Purity was estimated as greater than 96% by thin-layer chromatography, melting point, and NMR spectral analysis. thin-layer chromatography on $SiO_2$ in a mixture of methanol and ethyl acetate (3:7), with visualization by ultraviolet. A single spot with an Rf of 0.35 was seen.

EXAMPLE 3

Inhibition of Monoamine Oxidase A and B by N-(2-(5-Hydroxyindol-3-yl)ethyl)-3-(6-oxohydropurin-9-yl)propanamide Experiments were carried out to determine whether the serotonin analogue N-(2-(5-hydroxyindol-3-yl)ethyl)-3-(6-oxohydropurin-9-yl)propanamide (AIT-202) inhibited monoamine oxidases A and B. These experiments were performed as follows:

Mice (3–5 mice) were sacrificed by cervical dislocation. The brains were isolated and placed immediately in 10 ml cold isolation medium (IM) (500 μM EDTA, 5 mM HEPES, 0.25 M sucrose, and 10 mg/L bovine serum albumin (BSA)). The brains were minced and rinsed twice with 10 mL IM. The brains were then homogenized (5–6 strokes) in 10 mL IM. A volume (20 mL) of IM was then added and the homogenized preparation was centrifuged 8–10 minutes at 600×g at 4° C. The supernatant was transferred to a new tube. The pellet was resuspended in 30 mL IM and centrifuged again for 8 minutes at 600×g at 4° C. The supernatant was transferred to a new tube and the pellet discarded. Both supernatants were centrifuged for 10 min at 12,000×g at 4° C. The supernatant was discarded, the pellet was dislodged with a glass rod, and both pellets were resuspended in 5 mL IM and combined. A volume of IM (20 mL) was added and the suspension centrifuged for 10 min at 12,000×g at 4° C. The supernatants were discarded. The pellets were dislodged with a glass rod and resuspended in 2–4 mL IM and stored on wet ice during the course of the experiments.

The compounds tested were predissolved in dimethyl sulfoxide (DMSO) and further diluted with water as required.

For the enzyme assays, 1.0 mL to 1.5 mL 50 mM sodium phosphate, pH 7.4 containing 5 μM scopoletin and 2 U/mL horseradish peroxidase) were aliquoted in the wells of a Falcon 24-well plate (reaction mixture or RM). Mitochondrial protein (0.22–0.24 mg/mL final concentration) was added, and the reaction mixtures were preincubated approximately 6 minutes with 16 μM pargyline (monoamine oxidase B inhibitor) and 166 μM clorgyline (monoamine oxidase A inhibitor) or 2–150 μM of the tested serotonin analogue or the corresponding volume of water containing 1–5% DMSO respectively at 37° C. The preincubation was carried out in the Cytofluor® 4000 (PerSeptive Biosystems) and the baseline fluorescence at $\lambda_{ex}$=360 nm and $\lambda_{em}$=460 nm was recorded. After 6 min, the reading was interrupted and 150–166 μM tyramine (monoamine oxidase A and monoamine oxidase B substrate) or the corresponding amount of water were added according to the plate layout. The reading was continued for approximately 30 minutes at 3-minute intervals. The rate of the fluorescence decrease during this time was used to determine the effect of the tested compounds on the catalytic activity of both enzyme isoforms. Each plate contained a positive control containing the inhibitors for monoamine oxidase A or B respectively as well as a negative control without enzyme substrate. All determinations were in duplicates on the plate.

Determination of the protein concentration was carried out according to the manufacturer's instructions (Sigma, St. Louis, Mo.) for the bicinchoninic acid (BCA) protein determination.

Figure 2:
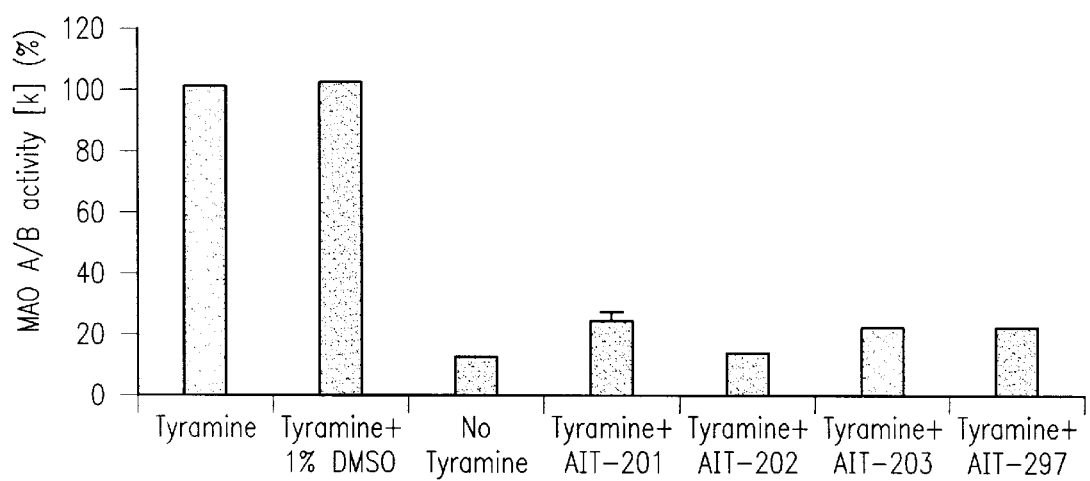
FIG. 2 is a graph showing the effect of 150 μM of N-(2-(5-hydroxyindol-3-yl)ethyl)-3-(6-oxohydropurin-9-yl) propanamide on the catalytic activity of monoamine oxidase A/B; the reaction mixture contained 150 μM substrate (tyramine) and 0.22 mg/mL mitochondrial protein.
Figure 3:
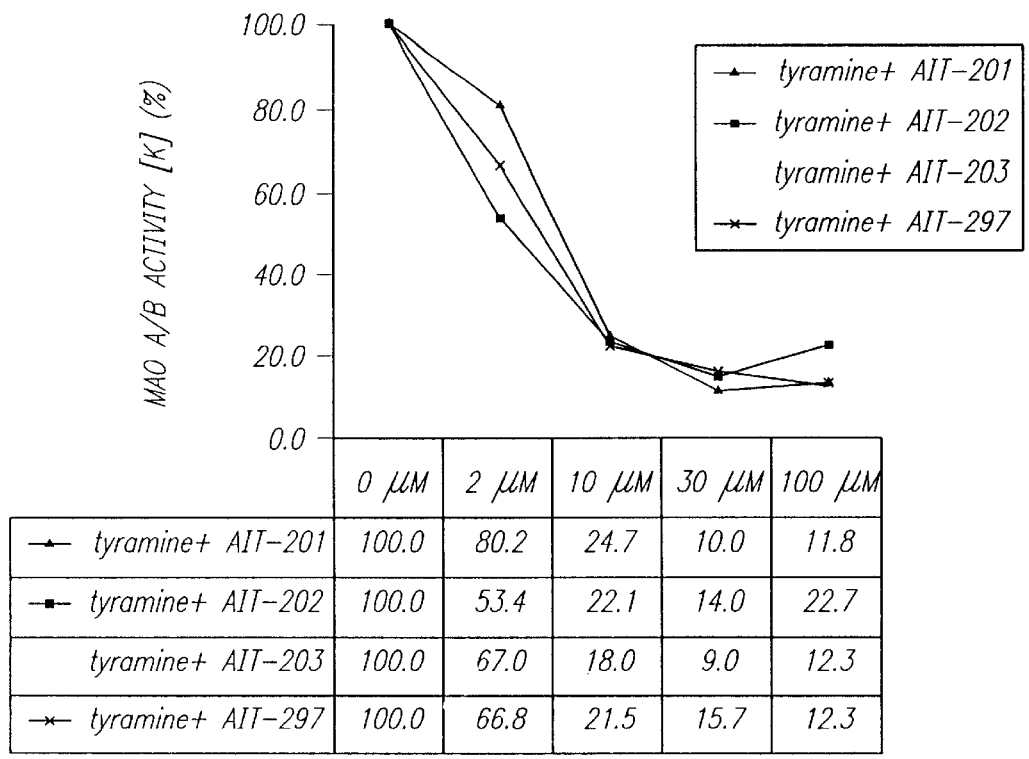
FIG. 3 is a graph showing the effects of increasing concentrations of N-(2-(5-hydroxyindol-3-yl)ethyl)-3-(6-oxohydropurin-9-yl)propanamide on the activity of monoamine oxidase A/B; concentrations tested were 0 μM, 2 μM, 10 μM, 20 μM, and 100 μM; the reaction mixture contained 166 μM substrate (tyramine) and 0.24 mg/mL mitochondrial protein.

The results are shown in FIGS. 2 and 3. For comparison, the experiments for which the results are shown in FIGS. 2 and 3 also included the 9-substituted hypoanthine derivatives that are dopamine analogues, N-(2-(3,4-dihydroxyphenyl)ethyl)-3-(6-oxohydropurin-9-yl)propanamide (designated as AIT-203); N-(2-hydroxy-2-(3,4-dihydroxyphenyl))ethyl-3-(6-oxohydropurin-9-yl)propanamide (designated as AIT-297); and N-(1-carboxyl-2-(3,4-dihydroxyphenyl))ethyl-3-(6-oxohydropurin-9-yl)propanamide (designated as AIT-201). For the results presented in FIG. 2, the reaction mixture contained 150 µM substrate (tyramine) and 0.22 mg/mL mitochondrial protein. For the results presented in FIG. 3, the reaction mixture contained 166 µM substrate (tyramine) and 0.24 mg/mL mitochondrial protein.

The $IC_{50}$ is estimated at 2.0 µM for this compound. Lyles et al. (J. Pharm. Pharmac. 26: 921–930 (1974)) reported an $IC_{50}$ of approximately 1.5 µM using rat heart mitochondria and tyramine as substrate.

This indicates a significant effect of the serotonin analogue on the catalytic activity of monoamine oxidase A and B. This is particularly important because a drug currently available for treatment of Parkinson's disease, a disease of dopaminergic neurons, selegiline, which has the chemical name (R)-(-)-N-2-dimethyl-N-2-propynyl-phenylethylamine hydrochloride, is a monoamine oxidase type B inhibitor. Moreover, this result is unexpected.

EXAMPLE 4

Activity of N-(2-(5-Hydroxyindol-3-yl)ethyl)-3-(6-oxohydropurin-9-yl)propanamide in Controlling Obesity The activity of N-(2-(5-hydroxyindol-3-yl)ethyl)-3-(6-oxohydropurin-9-yl)propanamide (AIT-202) in controlling obesity in mice was tested. Mice from the existing animal colony of NeoTherapeutics (Irvine, Calif.) which were naturally obese (greater than 45 grams in weight) were treated with N-(2-(5-hydroxyindol-3-yl)ethyl)-3-(6-oxohydropurin-9-yl)propanamide daily orally by gavage for 14 days. The mice were dosed with one of three doses of N-(2-(5-hydroxyindol-3-yl)ethyl)-3-(6-oxohydropurin-9-yl)propanamide or vehicle (0.5% methylcellulose). Their weight and food consumption were monitored daily.

Figure 4:
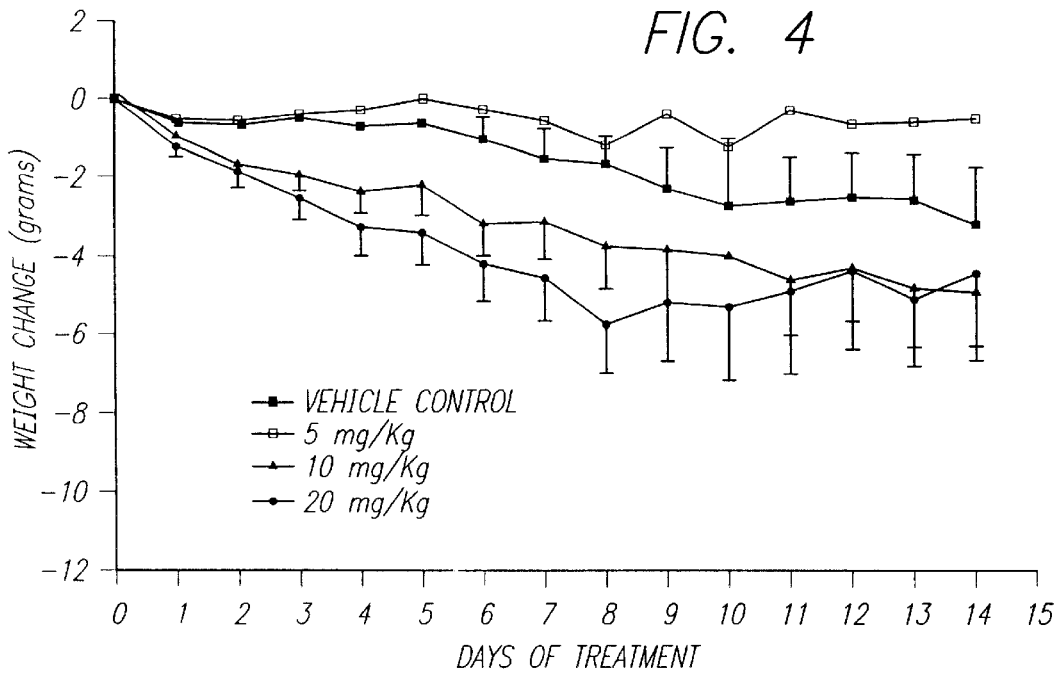
FIG. 4 is a graph showing the effects of increasing concentrations of N-(2-(5-hydroxyindol-3-yl)ethyl)-3-(6-oxohydropurin-9-yl)propanamide on the weight of obese mice during a 14-day course of treatment.

The results are shown in FIG. 4. There appears to be benefit to treatment with N-(2-(5-hydroxyindol-3-yl)ethyl)-3-(6-oxohydropurin-9-yl)propanamide in obese mice.

EXAMPLE 5

Activity of N-(2-(5-Hydroxyindol-3-yl)ethyl)-3-(6-oxohydropurin-9-yl)propanamide in Lowering Total Serum Cholesterol and in Raising HDL Cholesterol The activity of N-(2-(5-hydroxyindol-3-yl)ethyl)-3-(6-oxohydropurin-9-yl)propanamide (AIT-202) in lowering total serum cholesterol was tested in mice. Mice (5 mice) were administered N-(2-(5-hydroxyindol-3-yl)ethyl)-3-(6-oxohydropurin-9-yl)propanamide orally at a dosage of 300 mg/kg body weight for 24 hours before cholesterol determination. Total serum cholesterol was determined by standard methods. By comparison with a control group that did not have the 9-substituted hypoxanthine derivative administered, total serum cholesterol was decreased by 18% after administration of the derivative. A decrease of 15% or more is considered significant in this test.

To confirm this finding and to show that N-(2-(5-hydroxyindol-3-yl)ethyl)-3-(6-oxohydropurin-9-yl)propanamide acts to raise HDL cholesterol, which protects against cardiovascular disease, Swiss Webster mice were fed a high cholesterol diet or a normal diet for 7 days. On days 6 and 7 the mice were given the compound N-(2-(5-hydroxyindol-3-yl)ethyl)-3-(6-oxohydropurin-9-yl)propanamide (AIT-202), a positive control (bezafibrate), or a vehicle. The animals were fasted overnight and on day 8 trunk blood was collected. Total cholesterol and HDL cholesterol were measured in serum.

Figure 5:
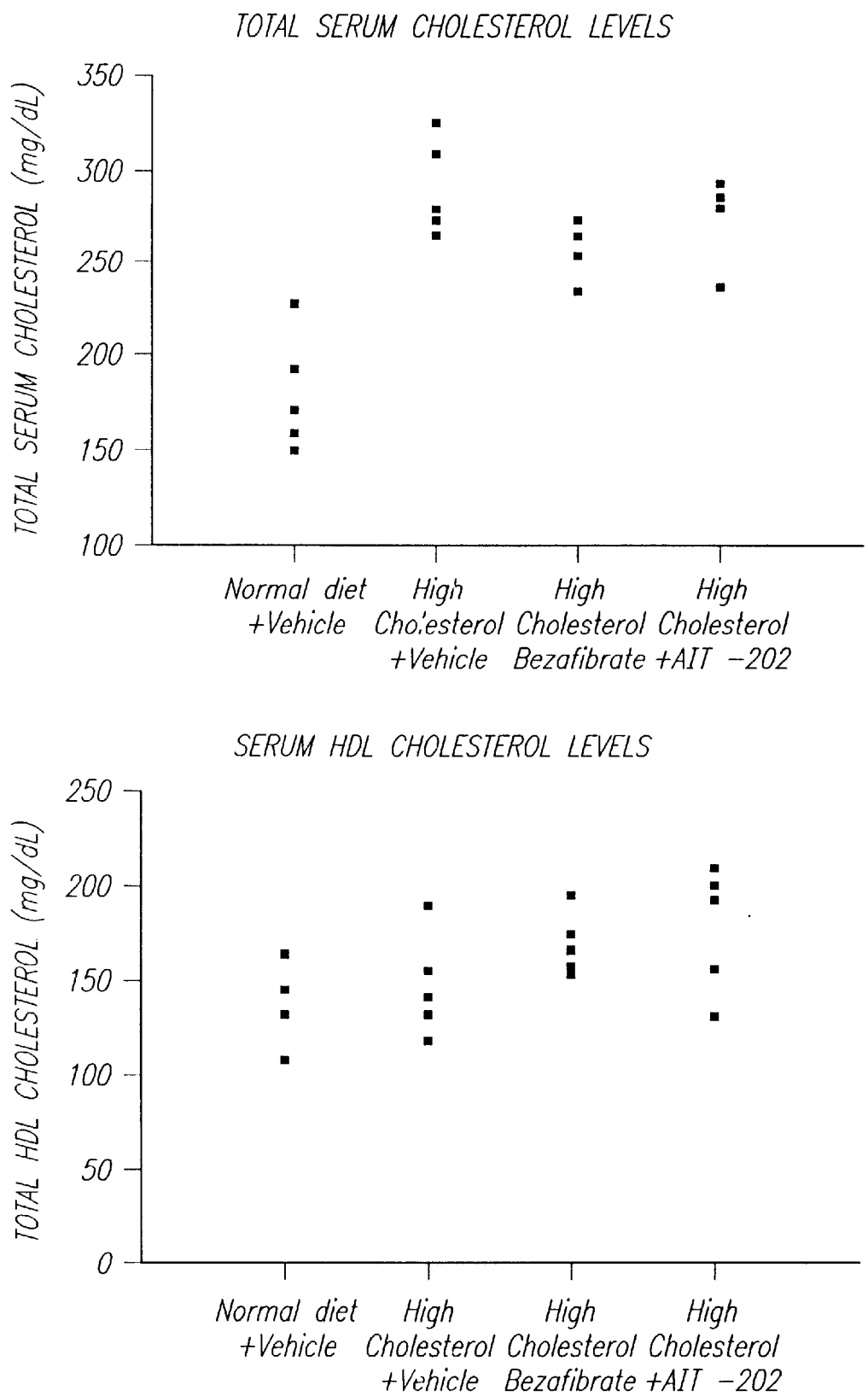
FIG. 5 is a graph showing levels of total serum cholesterol and HDL cholesterol in serum in rats fed a high cholesterol diet treated with bezafibrate or with N-(2-(5-hydroxyindol-3-yl)ethyl)-3-(6-oxohydropurin-9-yl)propanamide.

The results from a representative experiment are shown in FIG. 5. These results indicate that N-(2-(5-hydroxyindol-3-yl)ethyl)-3-(6-oxohydropurin-9-yl)propanamide both lowers total serum cholesterol and raises HDL cholesterol in a representative animal model.

ADVANTAGES OF THE INVENTION

The 9-substituted hypoxanthine derivatives of the present invention cross the blood-brain barrier efficiently and selectively and have unexpected activity as monoamine oxidase inhibitors. These derivatives therefore have use in treating conditions and diseases treatable with monoamine oxidase inhibitors. These derivatives also have other uses, such as in controlling obesity, lowering serum cholesterol levels, and increasing HDL cholesterol levels in serum.

Although the present invention has been described with considerable detail, with reference to certain preferred versions thereof, other versions and embodiments are possible. Therefore, the scope of the invention is determined by the following claims.

What is claimed is:

1. A 9-hypoxanthine derivative of formula (I) wherein the compound is N-(2-(5-hydroxyindol-3-yl)ethyl)-3-propanamide, where n is 2, $R_1$ is H, and $R_2$ is OH.

2. A pharmaceutical composition comprising:
    (a) an effective amount of a 9-substituted hypoxanthine derivative of formula (I) where n is an integer from 1 to 6, $R_1$ is selected from the group consisting of H, COOH, and $COOW_1$, where $W_1$ is selected from the group consisting of lower alkyl, amino, and lower alkylamino, and $R_2$ is selected from the group consisting of H and OH; and
    (b) a pharmaceutically acceptable carrier.

3. The pharmaceutical composition of claim 2 wherein the 9-substituted hypoxanthine derivative is the compound of formula (I) wherein n is 2.

4. The pharmaceutical composition of claim 3 wherein the 9-substituted hypoxanthine derivative is N-(2-(5-hydroxyindol-3-yl)ethyl)-3-(6-oxohydropurin-9-yl)propanamide.

5. The pharmaceutical composition of claim 3 wherein the 9-substituted hypoxanthine derivative is N-(2-(indol-3-yl)ethyl)-3-(6-oxohydropurin-9-yl)propanamide.

6. The pharmaceutical composition of claim 3 wherein the 9-substituted hypoxanthine derivative is N-(1-carboxyl)-(2-(5-hydroxyindol-3-yl)ethyl-3-(6-oxohydropurin-9-yl)propanamide.

7. A method of treating a disease or condition in a mammal treatable by inhibiting the activity of a monoamine oxidase comprising the step of administering an effective amount of a 9-substituted hypoxanthine derivative of formula (I) where n is an integer from 1 to 6, $R_1$ is selected from the group consisting of H, COOH, and $COOW_1$, where $W_1$ is selected from the group consisting of lower alkyl, amino, and lower alkylamino, and $R_2$ is selected from the group consisting of H and OH to the mammal.

8. The method of claim 7 wherein the 9-substituted hypoxanthine derivative is the compound of formula (I) wherein n is 2.

9. The method of claim 8 wherein the 9-substituted hypoxanthine derivative is N-(2-(5-hydroxyindol-3-yl)ethyl)-3-(6-oxohydropurin-9-yl)propanamide.

10. The method of claim 8 wherein the 9-substituted hypoxanthine derivative is N-(2-(indol-3-yl)ethyl)-3-(6-oxohydropurin-9-yl)propanamide.

11. The method of claim 8 wherein the 9-substituted hypoxanthine derivative is N-(1-carboxyl)-(2-(5-hydroxyindol-3-yl)ethyl-3-(6-oxohydropurin-9-yl)propanamide.

12. A method of treating obesity in a mammal comprising the step of administering an effective amount of a 9-substituted hypoxanthine derivative of formula (I) where n is an integer from 1 to 6, $R_1$ is selected from the group consisting of H, COOH, and $COOW_1$, where $W_1$ is selected from the group consisting of lower alkyl, amino, and lower alkylamino, and $R_2$ is selected from the group consisting of H and OH to the mammal.

13. The method of claim 12 wherein the 9-substituted hypoxanthine derivative is the compound of formula (I) wherein n is 2.

14. The method of claim 13 wherein the 9-substituted hypoxanthine derivative is N-(2-(5-hydroxyindol-3-yl)ethyl)-3-(6-oxohydropurin-9-yl)propanamide.

15. The method of claim 13 wherein the 9-substituted hypoxanthine derivative is N-(2-(indol-3-yl)ethyl)-3-(6-oxohydropurin-9-yl)propanamide.

16. The method of claim 13 wherein the 9-substituted hypoxanthine derivative is N-(1-carboxyl)-(2-(5-hydroxyindol-3-yl)ethyl-3-(6-oxohydropurin-9-yl)propanamide.

17. A method of lowering the level of serum cholesterol in a mammal comprising the step of administering an effective amount of a 9-substituted hypoxanthine derivative of formula (I) where n is an integer from 1 to 6, $R_1$ is selected from the group consisting of H, COOH, and $COOW_1$, where $W_1$ is selected from the group consisting of lower alkyl, amino, and lower alkylamino, and $R_2$ is selected from the group consisting of H and OH to the mammal.

18. The method of claim 17 wherein the 9-substituted hypoxanthine derivative is the compound of formula (I) wherein n is 2.

19. The method of claim 18 wherein the 9-substituted hypoxanthine derivative is N-(2-(5-hydroxyindol-3-yl)ethyl)-3-(6-oxohydropurin-9-yl)propanamide.

20. The method of claim 18 wherein the 9-substituted hypoxanthine derivative is N-(2-(indol-3-yl)ethyl)-3-(6-oxohydropurin-9-yl)propanamide.

21. The method of claim 18 wherein the 9-substituted hypoxanthine derivative is N-(1-carboxyl)-(2-(5-hydroxyindol-3-yl)ethyl-3-(6-oxohydropurin-9-yl)propanamide.

22. A method for increasing the level of HDL cholesterol in the blood serum of a mammal comprising the step of administering an effective amount of a 9-substituted hypoxanthine derivative of formula (I) where n is an integer from 1 to 6, $R_1$ is selected from the group consisting of H, COOH, and $COOW_1$, where $W_1$ is selected from the group consisting of lower alkyl, amino, and lower alkylamino, and $R_2$ is selected from the group consisting of H and OH.

23. The method of claim 22 wherein the 9-substituted hypoxanthine derivative is the compound of formula (I) wherein n is 2.

24. The method of claim 23 wherein the 9-substituted hypoxanthine derivative is N-(2-(5-hydroxyindol-3-yl)ethyl)-3-(6-oxohydropurin-9-yl)propanamide.

25. The method of claim 23 wherein the 9-substituted hypoxanthine derivative is N-(2-(indol-3-yl)ethyl)-3-(6-oxohydropurin-9-yl)propanamide.

26. The method of claim 23 wherein the 9-substituted hypoxanthine derivative is N-(1-carboxyl)-(2-(5-hydroxyindol-3-yl)ethyl-3-(6-oxohydropurin-9-yl)propanamide.

* * * * *